(12) United States Patent
Carron et al.

(10) Patent No.: US 8,123,523 B2
(45) Date of Patent: Feb. 28, 2012

(54) PROPHY ANGLE AND ADAPTER

(75) Inventors: Chris J. Carron, Bloomsdale, MO (US); David G. Grither, Ste. Genevieve, MO (US)

(73) Assignee: Angstrom Manufacturing, Inc., Bloomsdale, MO (US)

( * ) Notice: Subject to any disclaimer, the term of this patent is extended or adjusted under 35 U.S.C. 154(b) by 902 days.

(21) Appl. No.: 11/862,628

(22) Filed: Sep. 27, 2007

(65) Prior Publication Data

US 2008/0064007 A1   Mar. 13, 2008

Related U.S. Application Data

(63) Continuation-in-part of application No. 11/189,193, filed on Jul. 26, 2005, now Pat. No. 7,422,433, and a continuation-in-part of application No. 11/682,927, filed on Mar. 7, 2007, now abandoned.

(51) Int. Cl.
  *A61C 1/12* (2006.01)
(52) U.S. Cl. ............ 433/125; 433/126; 433/133
(58) Field of Classification Search .......... 433/103, 433/114, 115, 116, 118, 124, 125, 130, 131, 433/133, 165, 166, 126; 606/78–83, 167, 606/180
  See application file for complete search history.

(56) References Cited

U.S. PATENT DOCUMENTS

| | | | |
|---|---|---|---|
| 623,469 A | 4/1899 | Hailer | |
| 1,170,524 A | 2/1916 | Fernald | |
| 1,216,375 A * | 2/1917 | Sved | 433/130 |
| 1,333,809 A | 3/1920 | Laurer et al. | |
| 1,379,880 A | 5/1921 | Seaborn | |
| 1,534,817 A * | 4/1925 | Thiedemann et al. | 433/116 |
| 1,688,136 A * | 10/1928 | Chayes et al. | 279/76 |
| 1,999,488 A * | 4/1935 | Swisher et al. | 433/128 |
| 2,010,421 A * | 8/1935 | Terry | 433/126 |
| 2,025,779 A | 12/1935 | Roelke | |
| 2,400,912 A * | 5/1946 | Britt et al. | 433/82 |
| 3,509,629 A | 5/1970 | Kidokoro et al. | |
| 3,964,166 A | 6/1976 | Stahlman | |
| 4,053,983 A | 10/1977 | Flatland | |
| 4,266,933 A | 5/1981 | Warden et al. | |

(Continued)

FOREIGN PATENT DOCUMENTS

EP    1459696 A1    9/2004

OTHER PUBLICATIONS

US 5,883,201, 03/1999, Salem (withdrawn)

*Primary Examiner* — Todd Manahan
*Assistant Examiner* — Michael R Ballinger
(74) *Attorney, Agent, or Firm* — Steven M. Greenberg, Esq.; Carey, Rodriguez, Greenberg & O'Keefe

(57) ABSTRACT

A dental prophy angle includes a housing and a rotor. The housing defines a first bore and a second bore in communication with the first bore, and rotor is disposed within the second bore. The rotor includes a gearing system, and rotor includes a lock having a lock channel configured to receive a tip of a drive shaft. The housing includes a lock receiver for receiving the lock receiver permits rotation of the lock within the lock receiver and restrains linear movement of the lock in a direction substantially parallel to a rotational axis of the rotor.

7 Claims, 9 Drawing Sheets

U.S. PATENT DOCUMENTS

| | | | |
|---|---|---|---|
| 4,486,175 A | 12/1984 | Fisher et al. | |
| 4,522,595 A | 6/1985 | Selvidge | |
| 4,604,058 A | 8/1986 | Fisher et al. | |
| 4,929,180 A | 5/1990 | Moreschini | |
| 4,944,677 A | 7/1990 | Alexandre | |
| 5,028,233 A | 7/1991 | Witherby | |
| 5,040,978 A | 8/1991 | Falcon et al. | |
| 5,062,796 A | 11/1991 | Rosenberg | |
| 5,083,922 A | 1/1992 | Yale | |
| 5,120,220 A * | 6/1992 | Butler | 433/125 |
| 5,131,846 A | 7/1992 | Hall | |
| 5,156,546 A | 10/1992 | Frank et al. | |
| 5,156,547 A | 10/1992 | Bailey | |
| 5,209,658 A | 5/1993 | Brahler | |
| 5,211,560 A | 5/1993 | Lowder et al. | |
| 5,273,559 A | 12/1993 | Hammar et al. | |
| 5,316,475 A | 5/1994 | Rosenberg | |
| 5,328,369 A | 7/1994 | Bailey | |
| 5,340,310 A | 8/1994 | Bifulk | |
| 5,348,473 A | 9/1994 | Kivlighan, Jr. | |
| 5,360,339 A | 11/1994 | Rosenberg | |
| 5,374,189 A | 12/1994 | Mendoza | |
| 5,380,202 A | 1/1995 | Brahler | |
| 5,405,265 A | 4/1995 | Mendoza | |
| 5,423,679 A | 6/1995 | Bailey | |
| 5,433,605 A | 7/1995 | Strobl, Jr. | |
| 5,482,461 A | 1/1996 | Yale | |
| 5,484,284 A | 1/1996 | Bailey | |
| 5,496,218 A | 3/1996 | Brahler | |
| 5,503,555 A | 4/1996 | Bailey | |
| 5,507,644 A | 4/1996 | Kivlighan, Jr. | |
| 5,529,495 A | 6/1996 | Edwards | |
| 5,531,599 A | 7/1996 | Bailey | |
| 5,571,012 A | 11/1996 | Witherby et al. | |
| 5,584,690 A | 12/1996 | Maassarani | |
| 5,593,304 A | 1/1997 | Ram | |
| 5,645,426 A | 7/1997 | Grim et al. | |
| 5,683,247 A | 11/1997 | Bailey | |
| 5,690,488 A | 11/1997 | Spinello | |
| 5,692,901 A | 12/1997 | Roth et al. | |
| 5,730,595 A | 3/1998 | Bailey | |
| 5,743,718 A | 4/1998 | Mendoza et al. | |
| 5,749,728 A | 5/1998 | Bailey | |
| 5,766,008 A | 6/1998 | Hughes | |
| 5,775,905 A | 7/1998 | Weissenfluh et al. | |
| 5,797,744 A | 8/1998 | Rosenberg | |
| 5,871,353 A | 2/1999 | Pierce et al. | |
| 5,876,203 A | 3/1999 | Bailey | |
| 5,902,107 A | 5/1999 | Lowell | |
| 5,911,577 A | 6/1999 | Henrikson | |
| 5,924,864 A * | 7/1999 | Loge et al. | 433/118 |
| 5,941,705 A * | 8/1999 | Makris et al. | 433/141 |
| 5,964,590 A | 10/1999 | Loddeke et al. | |
| 6,012,922 A | 1/2000 | Novak | |
| 6,053,732 A | 4/2000 | Sale | |
| 6,083,000 A | 7/2000 | Charlton | |
| 6,089,866 A | 7/2000 | Brahler | |
| 6,099,309 A | 8/2000 | Cardarelli | |
| 6,146,140 A | 11/2000 | Bailey | |
| 6,149,430 A | 11/2000 | Nemetz et al. | |
| 6,168,433 B1 | 1/2001 | Hamlin | |
| 6,187,294 B1 | 2/2001 | Penner | |
| 6,203,322 B1 | 3/2001 | Kraenzle | |
| 6,247,931 B1 | 6/2001 | Postal et al. | |
| 6,257,886 B1 | 7/2001 | Warner | |
| 6,302,692 B1 | 10/2001 | Pond et al. | |
| 6,305,935 B1 | 10/2001 | Cardarelli | |
| 6,315,559 B1 | 11/2001 | Nakanishi | |
| 6,382,971 B1 | 5/2002 | Randolph | |
| 6,409,507 B1 | 6/2002 | Postal et al. | |
| 6,527,552 B2 | 3/2003 | Loddeke et al. | |
| 6,632,090 B1 | 10/2003 | Randolph | |
| 6,821,119 B2 | 11/2004 | Shortt et al. | |
| 6,875,017 B1 | 4/2005 | Tarr | |
| 7,153,133 B1 | 12/2006 | Chia et al. | |
| 2002/0009690 A1 * | 1/2002 | Kuhn et al. | 433/105 |

\* cited by examiner

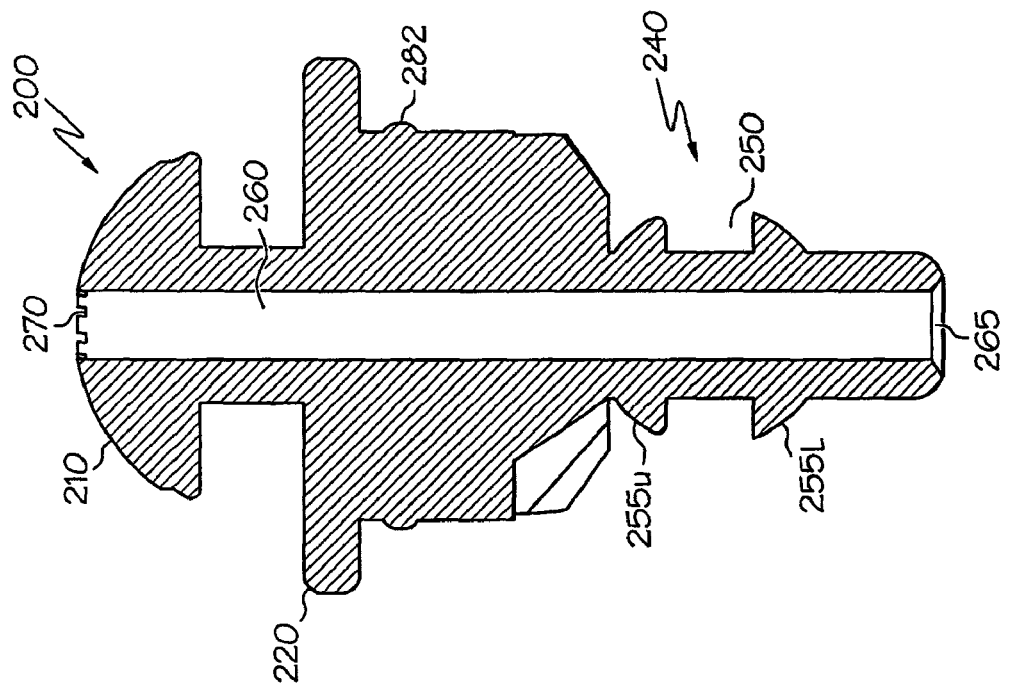
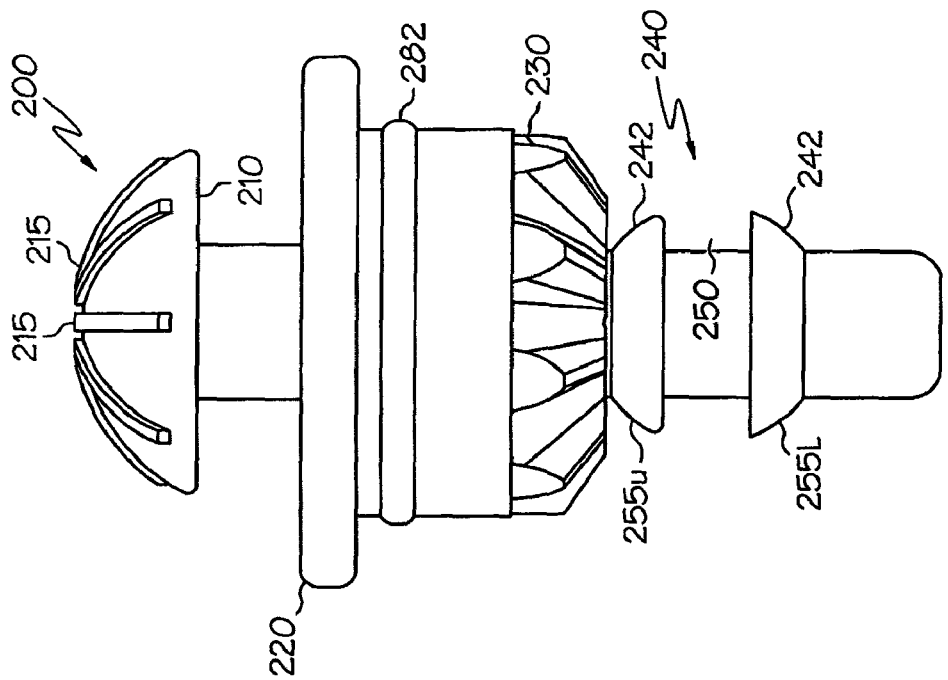
FIG. 2B
FIG. 2A

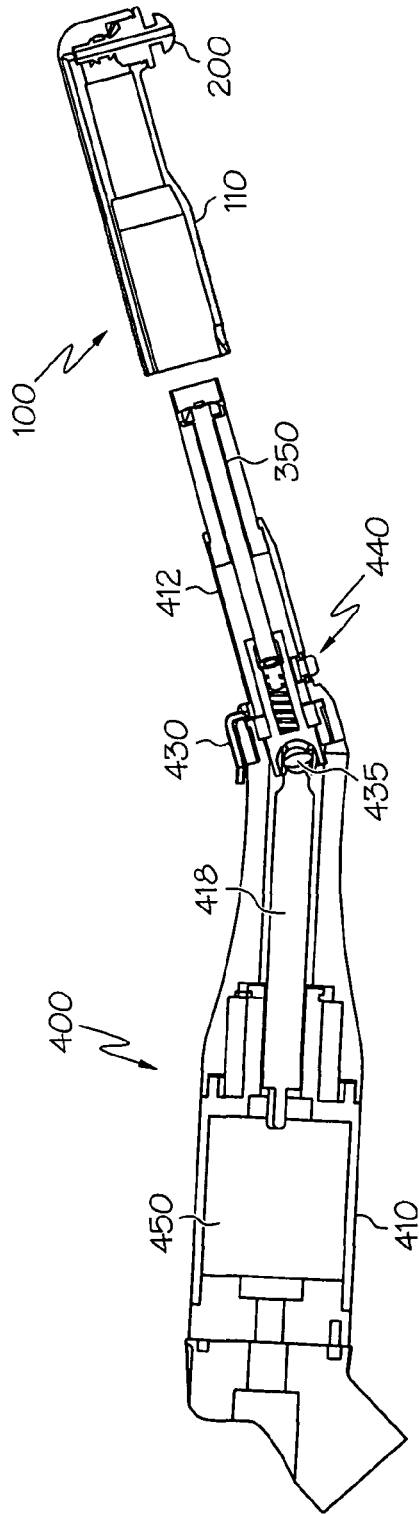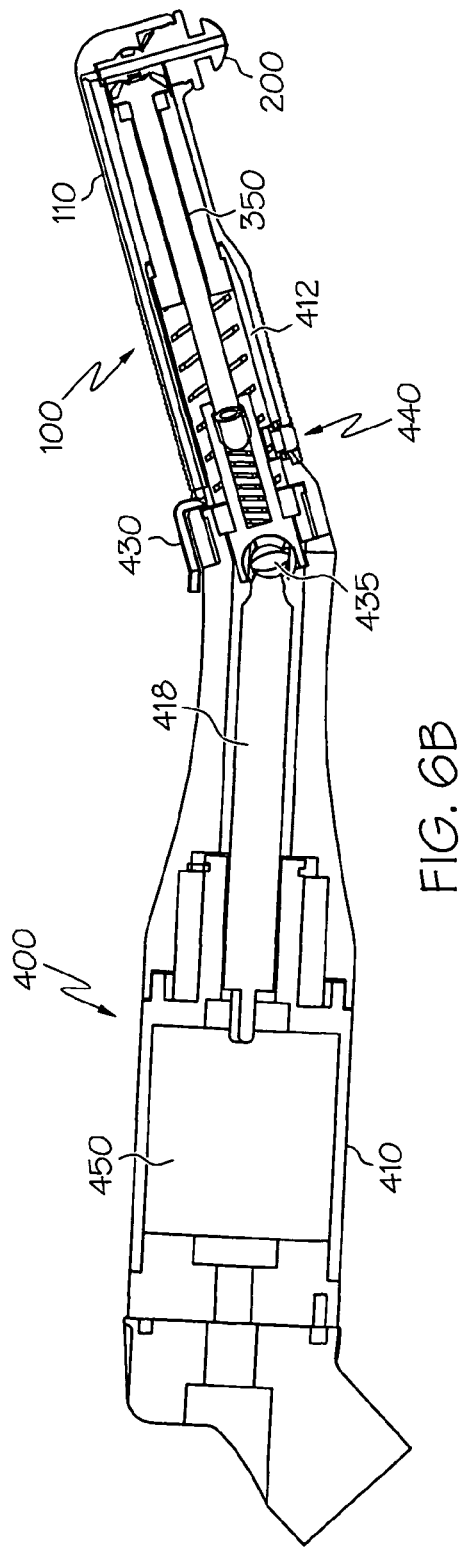

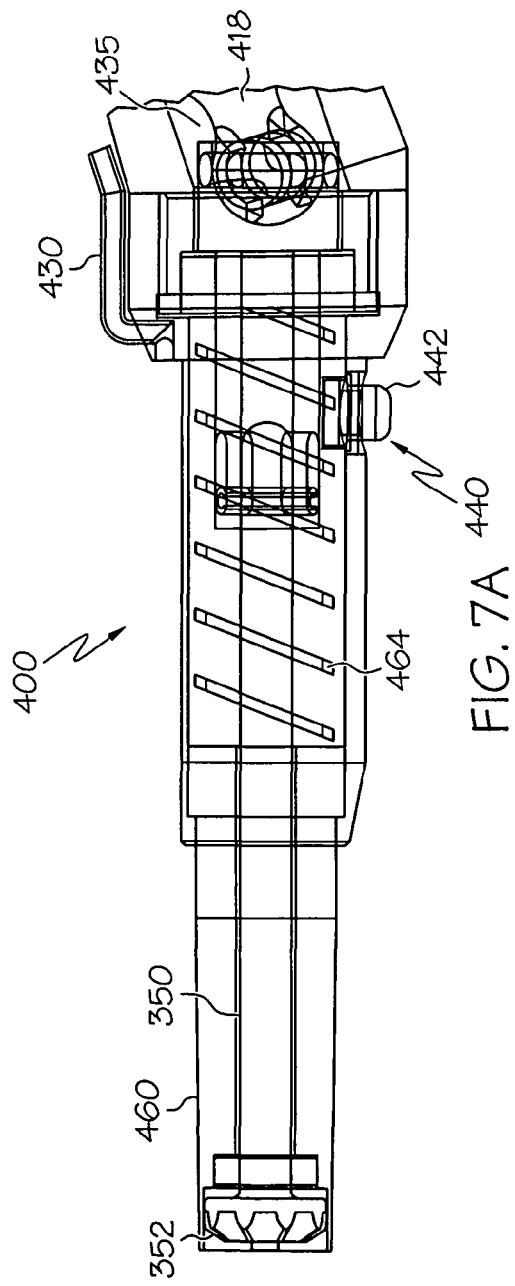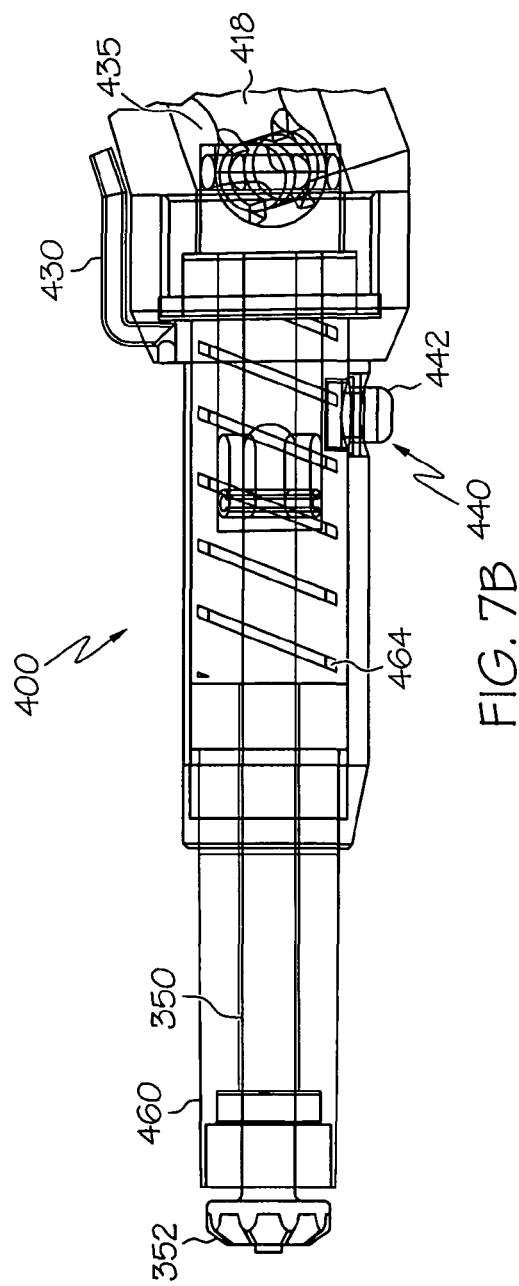

PROPHY ANGLE AND ADAPTER

CROSS-REFERENCE TO RELATED APPLICATIONS

This application is a Continuation-In-Part of U.S. application Ser. No. 11/189,193, filed on Jul. 26, 2005, now U.S. Pat. No. 7,422,433 and a Continuation-In-Part of U.S. application Ser. No. 11/682,927 filed on Mar. 7, 2007, now abandoned all of which are incorporated herein by reference in their entirety.

BACKGROUND OF THE INVENTION

1. Field of the Invention

The disclosure relates generally to dental instruments and, more specifically, to prophy angles and adapters for use with prophy angles.

2. Description of the Related Art

Dental prophylaxis angles, generally referred to as "prophy angles," are commonly used dental instruments for providing rotation for dental tools such as brushes, prophy cups, or other receptacles used in cleaning/polishing teeth. Referring to FIGS. 1A and 1B, a prophy angle 10 can include an inner housing 16 having an outer housing 18 and a rotor 14 extending at approximately a 90° angle to the neck 18, which increases the ability of a dentist to reach various surfaces of the teeth of a patient. A drive shaft or rotating member 12 can be located within the housing 16 and attached to a driven gear 20 in the head of the prophy angle. Prophy angles 10 are generally affixed to an adapter or hand piece (not shown), which connects the prophy angle to a drive source (not shown), thereby enabling a rotating motion of the rotating member 12 and driven gear 20 of the prophy angle and any affixed dental tool.

Prophy angles 10 are commonly manufactured from lightweight plastic to make them disposable, thereby increasing overall sterility in the dental environment. Being disposable, there is a desire to reduce the cost and/or complexity of assembly of the prophy angle 10 while, at the same time, maintaining the functionality and safety of the prophy angle 10.

One technique to reduce cost is to limit the number of separate pieces in the assembly of the prophy angle 10. For example, the prophy angle in FIG. 1B includes four separate pieces: (i) the rotating member 12, (ii) the inner housing 16, (iii) the outer housing 18, (iv) and the rotor 14. A reduced number of separate pieces requires less molds to form the separate pieces and less assembly of the pieces. However, by reducing the numbers of separate pieces, each individual and separate piece typically becomes more complex as each piece can take on more functions.

One of the issues preventing further reduction in the number of pieces in a disposable prophy angle 10 relates to the ability of the prophy angle 10 to maintain and restrain the position of the rotor 14 within the outer housing 16. Since the rotor 14 both engages the rotating member 12 and rotates at a head speed, the position of the rotor 14 within the outer housing 16 is critical to maintain a proper engagement between the rotating member and the rotor 14 and to prevent the rotor 14 from being unbalanced during rotation. An improperly positioned and/or restrained rotor 14 can cause failure of the prophy angle 10 and/or causes damage to the adaptor, the dental professional and/or the patient. There is, therefore, a need for an improved prophy angle that reduces the number of pieces in the prophy angle yet while maintaining the positional stability of the rotor within the outer housing.

BRIEF SUMMARY OF THE INVENTION

Embodiments of the invention provide a novel and non-obvious dental prophy angle. The dental prophy angle includes a housing and a rotor. The housing defines a first bore and a second bore in communication with the first bore, and rotor is disposed within the second bore. The rotor includes a gearing system, and rotor includes a lock having a lock channel configured to receive a tip of a drive shaft. The housing includes a lock receiver for receiving the lock, and the lock receiver permits rotation of the lock within the lock receiver and restrains linear movement of the lock in a direction substantially parallel to a rotational axis of the rotor. The lock includes a upper portion and a lower portion, and the upper portion and the lower portion define the channel. A seal is positioned between the housing and the rotor, and the second bore is adapted to removably receive the drive shaft.

In another embodiment of the invention, a dental adapter for a prophy angle includes a nose, a body connected to the nose, a drive shaft extending from the nose, and a slidable sleeve extending over at least a portion of the drive shaft. The drive shaft includes a gear. In a retracted position of the slidable sleeve, the gear is revealed, and in an extended position of the slidable sleeve, the slidable sleeve at least partially covers the gear. The drive shaft is linear movable relative to the body along a line substantially parallel to a longitudinal axis of the drive shaft. A resilient member is connected to the drive shaft for biasing the drive shaft along the line. The drive shaft includes a tip extending from a distal end of the drive shaft, and the tip is adapted to engage a rotor of the prophy angle. The adapter includes a drive source connected to the drive shaft by a coupler.

In yet another embodiment of the invention, a dental tool includes a prophy angle and an adapter for receiving and driving the prophy angle. The prophy angle includes a housing and a rotor, and the adapter includes a body, a drive shaft for driving the rotor, a slidable sleeve, and a nose for receiving the prophy angle. The rotor includes a lock having a lock channel configured to receive a tip of a drive shaft. The engagement of the lock channel and the tip restrains movement of the rotor lock in a direction towards the drive shaft and restrains movement of the lock relative to the tip in a direction substantially parallel to a rotational axis of the rotor. In a retracted position of the slidable sleeve, a gear of the drive shaft is revealed, and in an extended position of the slidable sleeve, the slidable sleeve at least partially covers the gear. The rotor includes a rotor conduit having an inlet and an outlet, the housing includes a housing conduit having an inlet and an outlet, and the adapter includes a supply conduit having an outlet. The outlet of the housing conduit is connected to the inlet of the rotor conduit, and the outlet of the supply conduit is releaseably connected to the inlet of the housing conduit.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein:

FIGS. 2A and 2B are, respectively, side and cross-sectional side views of the rotor;

FIGS. 6A and 6B are, respectively, exploded and assembled cross-sectional views of a prophy angle and adapter in accordance with the inventive arrangements;

FIGS. 7A and 7B are cross-sectional side views of the adapter with a sleeve, respectively, in extended and retracted positions, in accordance with the inventive arrangements.

DETAILED DESCRIPTION OF THE INVENTION

Figure 1A:
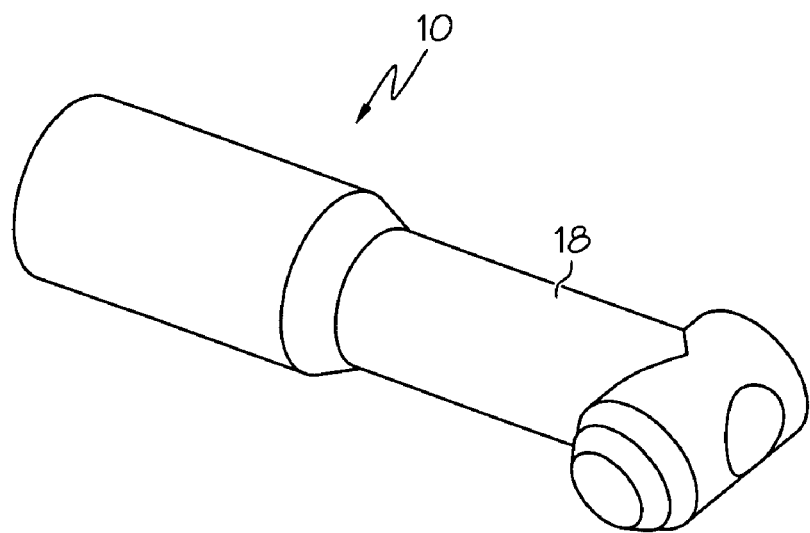
FIGS. 1A and 1B are, respectively, a perspective view and a side cross-sectional view of a prophy angle.
Figure 1B:
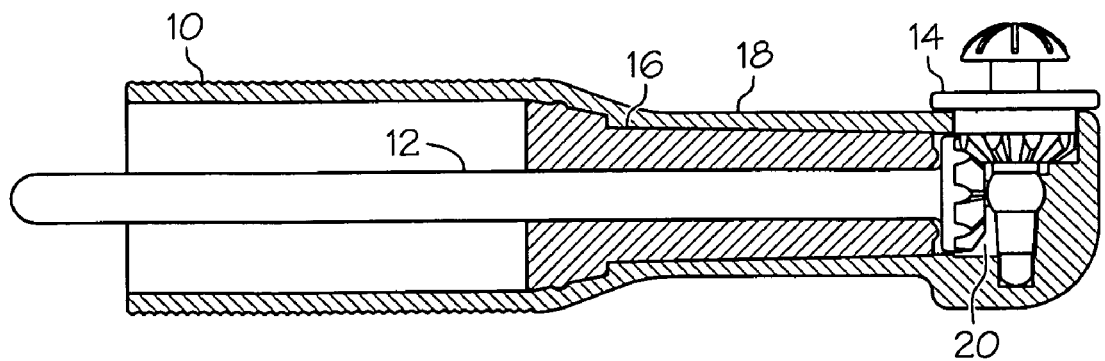

Referring to FIGS. 5A-5B and 6A-6B, a prophy angle 100 and adaptor 400 are disclosed. The prophy angle 100 includes a rotor 200 positioned within a housing 110. The prophy angle 100 is adapted to fit over a drive shaft 350 and engage the adaptor 400, and in certain aspects, the drive shaft 350 is part of the adaptor 400. In operation, the prophy angle 100 may be inserted onto and removed from the adaptor 400 so as to be considered disposable.

Referring to FIGS. 2A and 2B, the rotor 200 includes an attachment device 210 to which an attachment, such as a prophy cup (not shown), can be attached. Many types of attachment devices 210 are known as capable of connecting an attachment to a rotor 200, and the rotor 200 is not limited as to a particular type of attachment device 210 so capable. For example, the attachment device 210 may be a button. Although the button is not limited as to a specific shape or orientation, the button 210 may include additional protrusions 215 to accommodate a specific prophy cup. Another example of an attachment device 210 is a prophy cup with a threaded post molded inside.

The rotor 200 may include a radially-extending flange 220. In certain aspects of the rotor 200, the radially-extending flange 220 is sized to extend beyond an opening within the housing 110 (see FIG. 5B). The flange 220 of the rotor 200 may also be positioned over the opening to the second bore 114. In so doing, the flange 220 reduces the incidence of debris from the prophy cup or other attachment from entering the interior of the housing 110, which could potentially interfere with the subsequent operation of the prophy angle 100.

The rotor 200, while positioned within the second bore 114 (see FIGS. 5A and 5B), creates a seal 280 between the rotor 200 and an inner surface 134 of the second bore 114. Creating a seal between two surfaces is well known in the art, and any manner of creating a seal is acceptable for use with the prophy angle 100. However, in certain aspects of the prophy angle 100, one of the rotor 200 and the inner surface 134 of the second bore 114 includes an annular extension 282 and the other of the rotor 200 and the inner surface 134 includes an annular groove 182. Upon the rotor 200 being positioned within the second bore 114, the rotor 200 and/or the housing 110 deforms so as to permit the annular extension 282 to be inserted into the annular groove 182 and create the seal 280. The seal 280 also acts to restrain linear movement of the rotor 200 relative to the housing 110. Although not limited in this manner, upon the assembly of the rotor 200 with the housing 110, a lubricant may be added to ease the positioning of the rotor 200 within the housing 110 and/or reduce friction upon the rotor 200 rotating within the housing 110 during operation.

The rotor 200 includes a gearing system 230 to drive the rotation of the rotor 200 within the housing 110. Many types of gearing systems 230 are known capable of driving the rotation of the rotor 200 within the housing 110, and the rotor 200 is not limited as to a particular type of gearing system 230 so capable. However, in certain aspects of the rotor 200, the gearing system 230 includes one gear of a bevel gear set. As will be described in more detail below, the other gear 352 of the bevel gear set is attached to the drive shaft 350 (see FIG. 3) and is positionable within the housing 110.

Figure 4A:
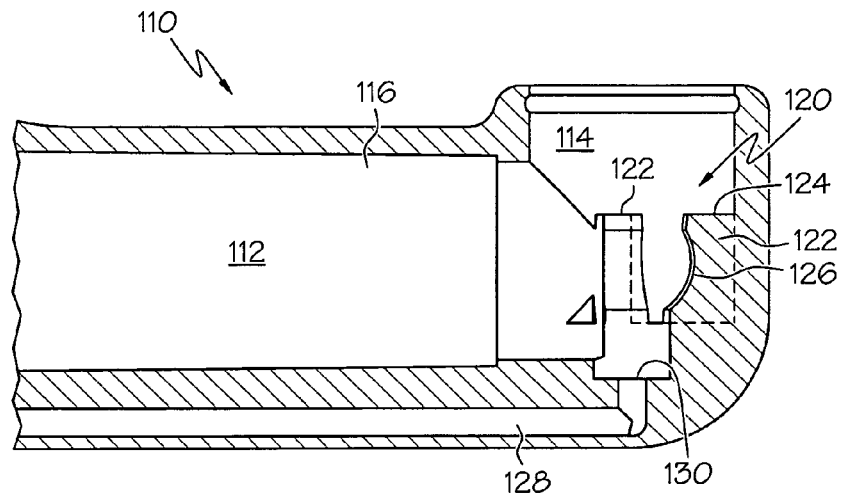
FIGS. 4A, 4B, and 4C are, respectively, cross-sectional side, rear, and top views of the housing.
Figure 4B:
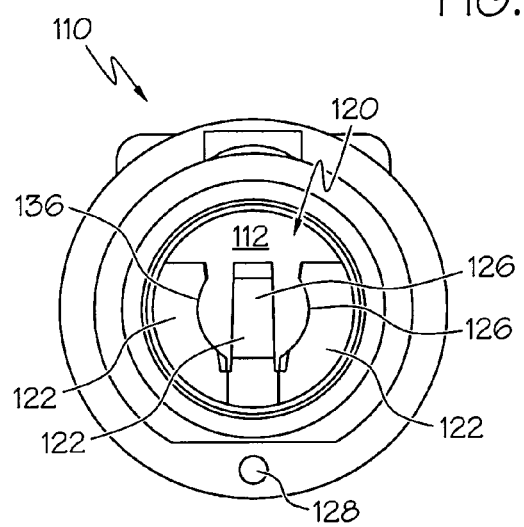
Figure 4C:
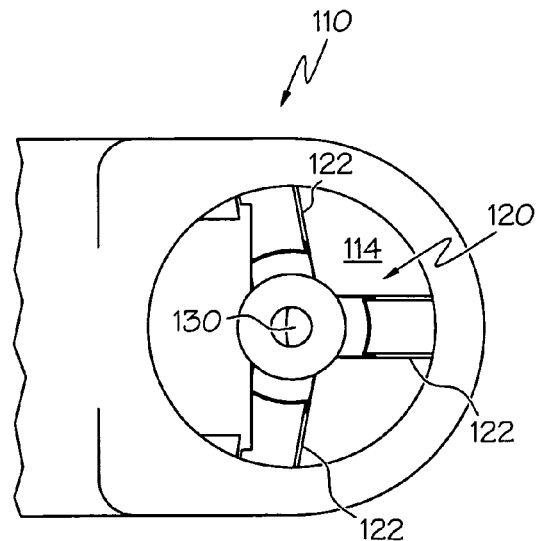

The rotor 200 also includes a lock 240. The lock 240 interacts with a lock receiver 120 (see FIGS. 4A-4C) of the housing 110 to restrain linear movement of the rotor 200 within the housing 110 yet allow rotation of the rotor 200 within the housing 110. In particular, the lock receiver 120 can restrain linear movement in a direction substantially parallel to a rotational axis of the rotor 200. In certain aspects of the lock 240, the lock 240 has a partially-curved outer profile 242. Also, portions of the lock 240 may have a substantially spherical profile 242 taken along a cross-section perpendicular to a longitudinal axis of the rotor 200. In so doing, the lock 240 interacts with the lock receiver 120 of the housing 110 to allow rotation of the rotor 200 within the housing 1 10.

The rotor 200 may also include a rotor conduit 260 having an inlet 265 and an outlet 270, and the prophy angle 100 is not limited as to the particular use of the rotor conduit 260. For example, the rotor conduit 260 may be used to transfer materials (e.g., dentifrice, water) to a working area of the prophy angle 100. Alternatively, the rotor conduit 260 may be used as part of a system to provide suction to the working area of the prophy angle 100.

Figure 3:
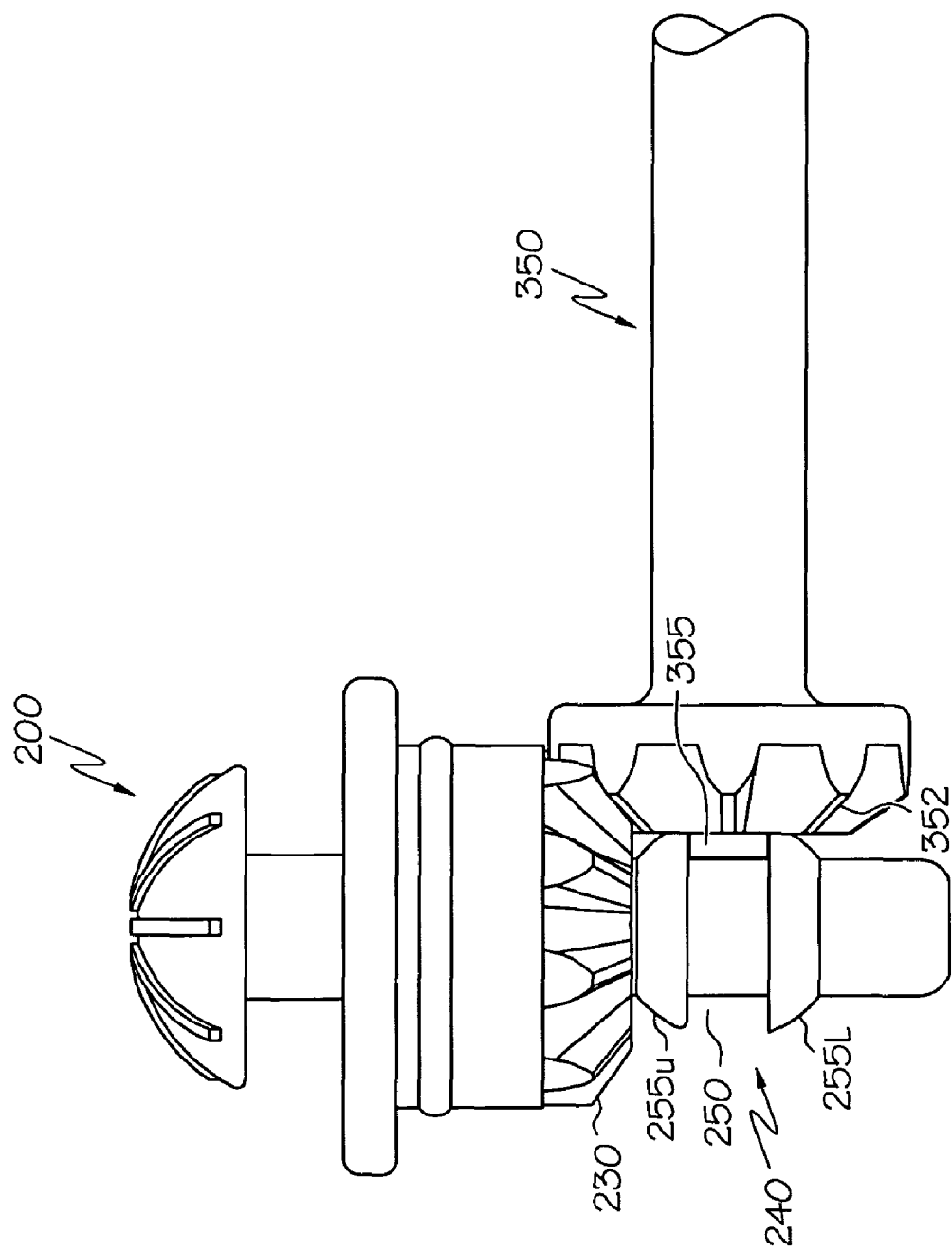
FIG. 3 is a cross-sectional side view of a drive shaft engaging the rotor, in accordance with the inventive arrangements.

Referring to FIG. 3, in certain aspects of the rotor 200, the lock 240 includes a recessed lock channel 250 for receiving a tip 355 extending from a distal end of a drive shaft 350. Upon the drive shaft 350 being engaged within the lock 240, the tip 355 is positioned within the lock channel 250. While so positioned, engagement between the tip 355 and upper and lower portions 255U, 255L of the lock 240 can restrict movement of the lock 240, respectively, in a downward direction and an upward direction. Moreover, a width of the lock channel 250 between the upper and lower portions 255,U 255L can be dimensioned slightly greater than a diameter of the tip 355 to further restrict movement of the lock 240 relative to the tip 355 and vice versa.

Although the lock 240 is illustrated as having both an upper portion 255U and a lower portion 255L, the lock 240 is not limited in this manner. For example, the lock 240 may only include the lower portion 250L, which would restrain movement of the lock 240 in the upward direction. The drive shaft 350 also restricts movement of the lock 240 in a direction towards the drive shaft 350.

In certain aspects of the rotor 200, however, the lock 240 includes both an upper portion 255U and a lower portion 255L. These two portions 255U, 255L, acting together, can restrain rotation of the drive shaft 350 about a specified axis of rotation and position the drive shaft 350 within the specified axis of rotation. The drive shaft 350 typically rotates at a high speed, and any imbalance of the drive shaft 350 can cause the drive shaft 350 to wobble during rotation, which can damage the drive shaft 350 and/or prophy angle 100 and/or cause poor engagement between the drive shaft 350 and the gearing system 230. However, by constraining the distal end (i.e., the tip 355) of the drive shaft 350 with the upper and lower portions 255U, 255L of the lock 240, this wobble, if present, can be reduced.

A further discussion of engagement of the rotor 200 and the drive shaft 350 and between the rotor and the housing 110 and the configurations thereof is found in related U.S. application Ser. No. 11/189,193, filed on Jul. 26, 2005, incorporated herein by reference in its entirety.

Referring to FIGS. 4A-4C and 5A-5B, the housing 110 is illustrated. The housing 110 includes a first bore 112 and a second bore 114. The first bore 112 extends along a longitudinal length of the of housing 110 and is configured to receive the drive shaft 350 (see FIG. 6B). The second bore 114 communicates with and extends substantially perpendicular from the first bore 112. The second bore 114 is also configured to receive the rotor 200. Although not limited in this manner, the housing 110 can be constructed from a variety of available plastics having sufficient rigidity to apply pressure to a patient's teeth, while remaining flexible enough to receive the internal components of the prophy angle.

The first bore 112 may also be configured to receive the adapter 400 (see FIG. 6B). Although not limited in this manner, the inner surface 116 of the first bore 112 may define a first shoulder 118 that limits movement of a portion of the adapter 400 past the shoulder 118. The adapter 400 engaging the first shoulder 118 may also be used to specifically position the adapter 400 and, thus, the drive shaft 350, within the housing 110. Other features capable of specifically positioning the adapter 400 within the housing 110 are known and can be used with the present adapter 400 and housing 110.

Positioned within the second bore 114 is a lock receiver 120. The lock receiver 120 receives the lock 240 of the rotor 200 and acts to restrain linear movement of the rotor 200 within the housing 110 yet allow rotation of the rotor 200 within the housing 110. In certain aspects, the lock receiver 120 includes a plurality of bearing arms 122 positioned within the second bore 114. The bearing arms 122 may include an upper bearing surface 124 and also a recess 126 on a radially inward-facing surface of the bearing arm 122. The recess 126 may have a profile configured to receive the lock 240 of the rotor 200.

The housing 110 may also include a housing conduit 128 having an outlet 130 that releaseably connects with the inlet 265 of the rotor conduit 260. The housing conduit 128 also includes an inlet 132 that is configured to be releaseably connected to the adapter 400.

Figure 5A:
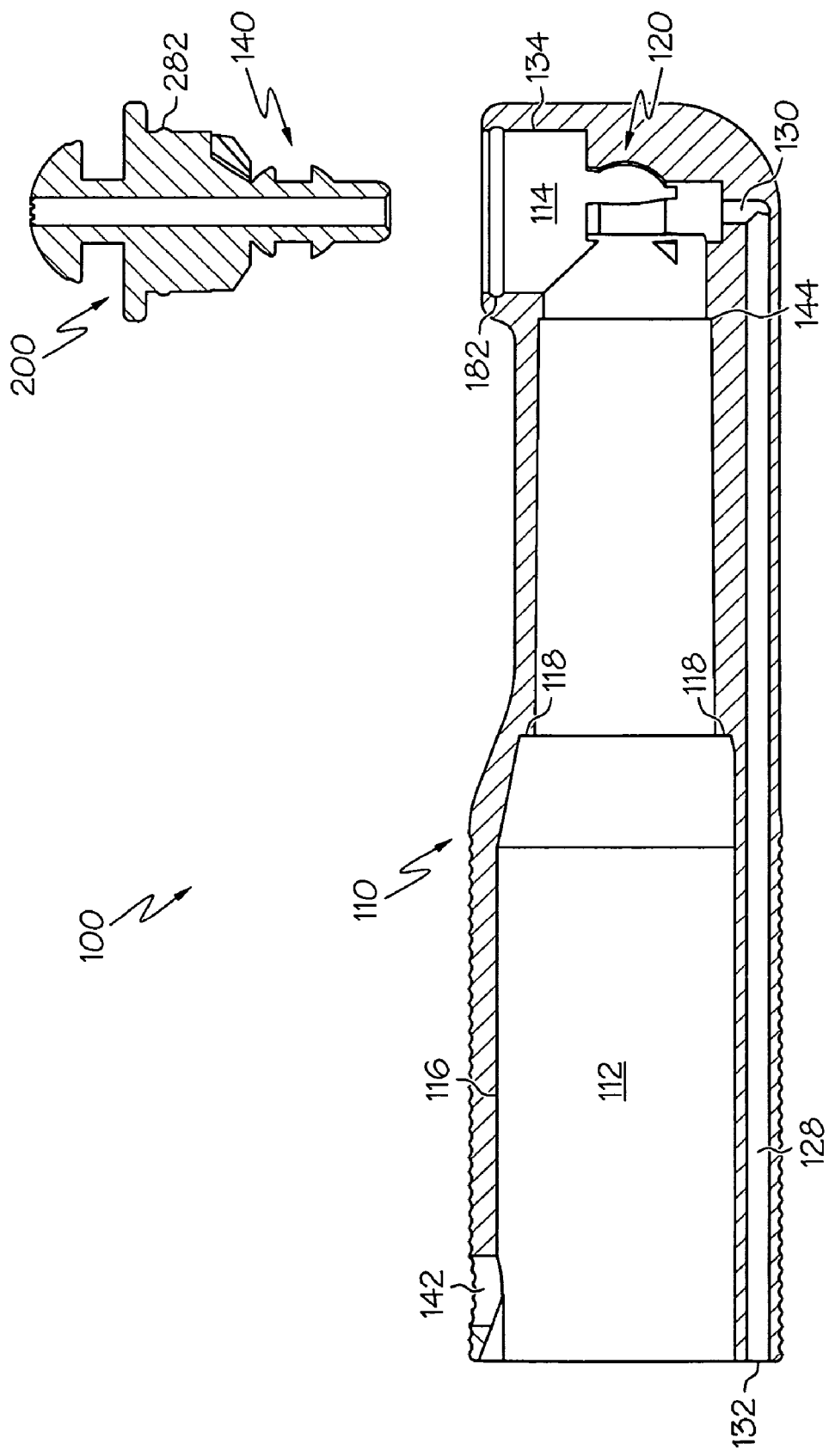
FIGS. 5A and 5B are, respectively, exploded and assembled cross-sectional side views of a housing and a rotor in accordance with the inventive arrangements.
Figure 5B:
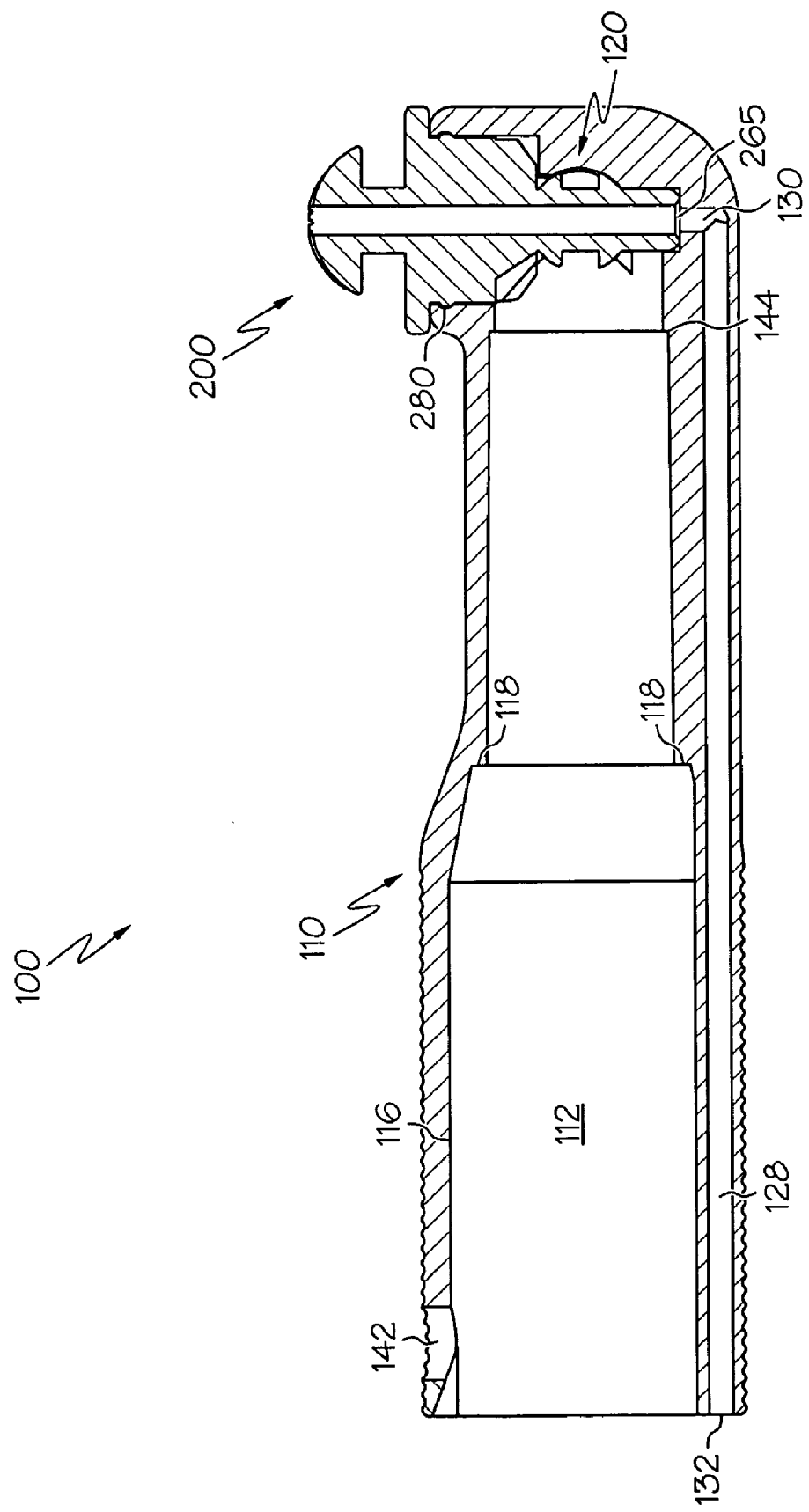

Referring specifically to FIGS. 5A and 5B, the prophy angle 100 is assembled by inserting the rotor 200 into the second bore 114. Upon the rotor 200 being positioned within the second bore 114 of the housing 110, the lock 140 of the rotor 200 is nested within the lock receiver 120 of the housing 110. As previously described, upon the lock 140 being nested within the lock receiver 120, movement of the rotor 200 out of the second bore 114 is restrained. Also, upon insertion of the rotor 200 within the second bore 114, the seal 280 between the rotor 200 and the inner surface 134 of the second bore 114 engages, which can further restrain movement of the rotor 200 out of the second bore 114. By restraining movement of the rotor 200 out of the second bore 114, a user can handle/manipulate the prophy angle 100 with reduced fear that the prophy angle 100 will become unintentionally disassembled.

Referring to FIGS. 6A and 6B, the prophy angle 100 is shown being assembled with an adapter 400, and FIGS. 7A and 7B illustrate the adaptor 400. The adapter 400, directly or indirectly, provides the rotational movement to the gearing system 230 of the rotor (see FIG. 3), and any adapter 400 so capable is acceptable for use with the prophy angle 100. The adaptor 400 includes a body 410 and a nose 412, and the nose 412 may be removably attachable to the body 410. Alternatively, the nose 412 may be integral with the body 410. The adapter 400 includes a shaft 418 that is connected to a drive shaft 350 via a coupler 435. The adaptor 400 may also include a supply conduit 430 (see FIGS. 7A and 7B) that is releaseably connectable to the inlet 132 of the housing conduit 128.

An outer portion of the nose 412 may be shaped to mate with the prophy angle 10. As is known in the art, many types of different types of prophy angles 100 exist that have different mating profiles, and the present adaptor 400 is not limited as to a particular shape of the nose 412 and as to a particular profile of prophy angle 100 with which the nose 412 can mate. However, in a current aspect of the adapter 400, the nose 412 is a configured as a doriot-style adapter. Depending upon the type of prophy angle 100, other type of connections devices include, but are not limited to, latch type, 3-ball chuck, attachment ring, push chuck, quick-connect collars, autochucks, E-type (i.e., ISO 3964), DIN 13940, ISO 1797, U-type, NSK type, and Midwest type.

The shaft 418 is rotated by the drive source 450. As is known in the art, many different types of drive sources 450 exist and these different drive sources 450 have different configurations for coupling with a rotating member, such as the shaft 418. In this regard, the present adapter 400 is not limited as to drive source 450 for the adapter 400. For example, the drive source 450 may be connectable to the adapter 400. Alternatively, the drive source 450 may be integrated with the adapter 400. Also, examples of drive sources 450 include electrically-driven and pneumatically-driven motors. A further discussion on adapters 400 and connections between the shaft 418 and either the drive source 450 or between the shaft 418 and the drive shaft 350 (e.g., via the coupler 435) is found in related U.S. application Ser. No. 11/682,927 filed on May 7, 2007, incorporated herein by reference in its entirety.

As illustrated, the drive shaft 350 is a part of the adaptor 400. However, the drive shaft 350 is not limited in this manner. For example, the drive shaft 350 may be a portion of the prophy angle 100. In other aspects, the drive shaft 350 is removably attachable to a collet within the adaptor 400. In so doing, the drive shaft 350 can be replaceable and/or cleaned.

The adaptor 400 may include a retention device 440 for maintaining a position of the prophy angle 100 on the adaptor 400 and any retention device 440 so capable is acceptable for use with the adaptor 400. In certain aspects of the adaptor 400, however, the retention device 440 is a locking pin 442 that is positionable within an opening 142 (see FIGS. 5A-5B) in the housing 110 of the prophy angle 100. The locking pin 442 may be resiliently biased such that after the locking pin 442 is depressed, to either allow the prophy angle 100 to be positioned over the adapter 400 or to remove the prophy angle 100 from the adapter 400, the locking pin 442 returns to an extended position. Upon the locking pin 442 being positioned within the opening 142, the locking pin 442 prevents removal of the prophy angle 100 from the adaptor 400.

Referring to specifically to FIGS. 7A and 7B, a slidable sleeve 460 may be positioned over the drive shaft 350. The slidable sleeve 460 moves from an extended position (FIG. 7A), which conceals the gear 352 of the drive shaft 350, to an retracted position (FIG. 7B), which reveals the gear 352 of the drive shaft 350. The slidable sleeve 460 is not limited in the manner in which the slidable sleeve 460 moves from the extended position to the retracted position and back again. However, in certain aspects, the slidable sleeve 460 engages a second shoulder 144 (see FIGS. 5A-5B) of the housing 110 as the slidable sleeve 460 is inserted into the housing 110, which causes the slidable sleeve 460 to retract relative to the gear 352 of the drive shaft 350.

The slidable sleeve 460 may also be connected to a resilient member 464, such as a spring, which is compressed upon the slidable sleeve 460 is retracted. Upon the slidable sleeve 460 being removed from the housing 110, the resilient member 464 biases the slidable sleeve 460 into the extended position. In this manner, upon the adapter 400 being completely removed from the housing 110, even unintentionally, the gear 352 of the drive shaft 350 is not exposed.

Figure 8:
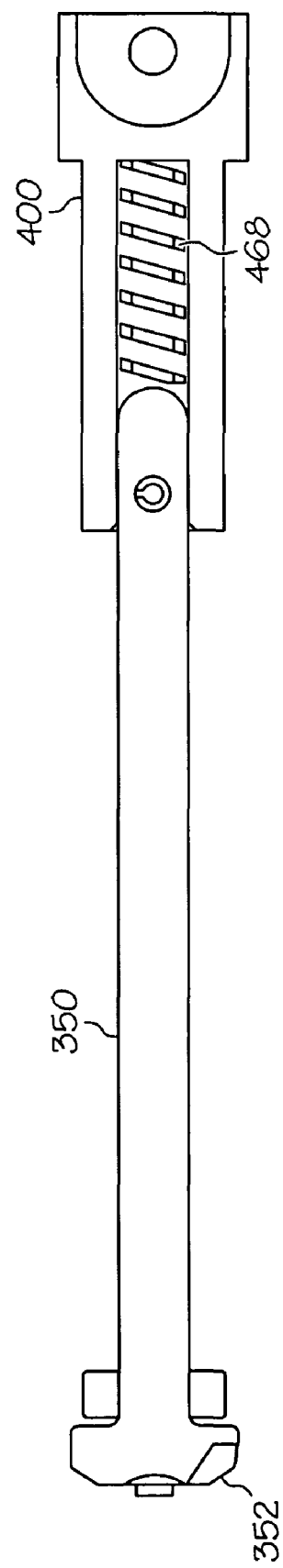
FIG. 8 is a cross-sectional side view of a portion of the adapter and the drive shaft.

Referring to FIG. 8, while attached to the adaptor 400, the drive shaft 350 may be capable of being biased along a line substantially parallel to a longitudinal axis of the drive shaft 350. Although any technique of enabling the drive shaft 350 to be biased is acceptable for use, similar to the slidable sleeve 460, the drive shaft 350 may be connected to a second resilient member 468, such as a spring.

Upon being inserted into the housing 110, the drive shaft 350 engages the gearing system 230, which biases the drive shaft 350 towards the adaptor 400. The second resilient member 468, in turn, pushes back against the drive shaft 350, which ensures proper engagement of the gear 352 of the drive shaft with the gear system 230 of the rotor 200. The ability of the drive shaft 350 to be biased along the line substantially parallel to the longitudinal axis of the drive shaft 350 gives the drive shaft 350 linear adjustability relative to the body 410 of the adaptor 400, and this linear adjustability allows for variations in dimensions in the housing 110, rotor 200, drive shaft 350 and/or adaptor 400.

What is claimed is:

1. A dental tool, comprising:
a prophy angle; and
an adapter for receiving and driving the prophy angle, wherein
the prophy angle includes a housing and a rotor, and
the adapter includes a body, a drive shaft for driving the rotor, a slidable sleeve, and a nose for receiving the prophy angle, wherein
the rotor includes a lock,
the housing includes a lock receiver for receiving the lock,
the lock receiver permitting rotation of the lock within the lock receiver and restraining linear movement of the lock in a direction substantially parallel to a rotational axis of the rotor and towards an opening in the housing, wherein
the lock having a lock channel configured to receive a tip of a drive shaft,
the engagement of the lock channel and the tip restraining movement of the rotor in a direction towards the drive shaft and restraining movement of the rotor in the direction substantially parallel to the rotational axis of the rotor, wherein
in a retracted position of the slidable sleeve, a gear of the drive shaft is revealed, and
in an extended position of the slidable sleeve, the slidable sleeve at least partially covers the gear.

2. The dental tool of claim 1, wherein
the drive shaft is linearly movable relative to the body along a line substantially parallel to a longitudinal axis of the drive shaft.

3. The dental tool of claim 1, wherein
the rotor includes a rotor conduit having an inlet and an outlet,
the housing includes a housing conduit having an inlet and an outlet,
the adapter includes a supply conduit having an outlet,
the outlet of the housing conduit is connected to the inlet of the rotor conduit, and
the outlet of the supply conduit is releasably connected to the inlet of the housing conduit.

4. The dental tool of claim 1, wherein
the lock includes a upper portion and a lower portion,
the upper portion and the lower portion define the lock channel.

5. The dental tool of claim 1, wherein
the prophy angle includes a seal positioned between the housing and the rotor.

6. The dental tool of claim 1, wherein
the lock receiver includes a plurality of bearing arms configured to receive the lock.

7. The dental tool of claim 6, wherein
each bearing arm includes a radially inward-facing surface having a recess.

* * * * *

UNITED STATES PATENT AND TRADEMARK OFFICE
CERTIFICATE OF CORRECTION

| | | |
|---|---|---|
| PATENT NO. | : 8,123,523 B2 | Page 1 of 1 |
| APPLICATION NO. | : 11/862628 | |
| DATED | : February 28, 2012 | |
| INVENTOR(S) | : Chris J. Carron and David G. Grither | |

It is certified that error appears in the above-identified patent and that said Letters Patent is hereby corrected as shown below:

Title Page, Item (57) Abstract:

- in the abstract, lines 6 - 10 reads as "the housing includes a lock receiver for receiving the lock receiver permits rotation of the lock within the lock receiver and restrains linear movement of the lock in a direction substantially parallel to a rotational axis of the rotor." Please add "and the lock" between "lock" and "receiver" at line 7, so the sentence reads as "The housing includes a lock receiver for receiving the lock and the lock receiver permits rotation of the lock within the lock receiver and restrains linear movement of the lock in a direction substantially parallel to a rotational axis of the rotor."

- move the comma between the number 255 and at the letter "U" at column 4, line 60, so to read "255U, 255L"

- replace "application Ser. No. 11/189,193, filed on Jul. 26, 2005" with the words "Patent No. 7,422,433" at column 5, line 20

- replace the word "an" with the word "a" at column 7, line 8

Signed and Sealed this
Sixth Day of November, 2012

David J. Kappos
*Director of the United States Patent and Trademark Office*